Figure 1:
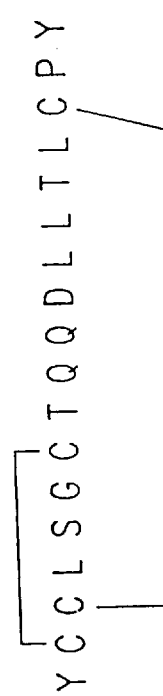

United States Patent [19]
Schwabe et al.

[11] Patent Number: 5,911,997
[45] Date of Patent: Jun. 15, 1999

[54] RELAXIN-LIKE FACTOR AND METHODS AND USES THEREOF

[75] Inventors: Christian Schwabe, Charleston, S.C.; Elaine Unemori, Oakland, Calif.

[73] Assignee: Connetics Corporation, Palo Alto, Calif.

[21] Appl. No.: 08/484,219

[22] Filed: Jun. 7, 1995

[51] Int. Cl.$^6$ .......................... A61K 38/22; C07K 14/575
[52] U.S. Cl. .......................... 424/198.1; 514/2; 530/303
[58] Field of Search .......................... 530/303; 424/198.1; 514/2

[56] References Cited

PUBLICATIONS

Adham, et al., 1993, "Cloning of cDNA for a Novel Insulin–like Peptide of the Testicular Leydig Cells", *J. Biol. Chem.* 268:26668–26672.

Adler, et al., 1973, "Circular Dischroism and Optical Rotatory Dispersion of Proteins and Polypeptides", *Methods Enzymol.* 27:675–735.

Büllesbach, et al., 1994, "Synthesis and biological properties of guinea pig relaxin". *Endocrine*. 2:1115–1120.

Büllesbach and Schwabe, 1994, "Total Synthesis of Human Relaxin and Human Relaxin Derivatives by Solid–phase Peptide Synthesis and Site–directed Chain Combination", *J. Biol. Chem.* 269:13124–13128.

Büllesbach and Schwabe, 1993, "Mouse Relaxin: Synthesis and Biological Activity of the First Relaxin With an Unusual Crosslinking Pattern", *Biochem. Biophys. Res. Commun.* 196:311–319.

Büllesbach and Schwabe, 1992, "The Receptor–binding Site of Human Relaxin II", *J. Biol. Chem.* 267:22957–22960.

Büllesbach and Schwabe, 1991, "Total Synthesis of Human Relaxin and Human Relaxin Derivatives by Solid–phase Peptide Synthesis and Site–directed Chain Combination", *J. Biol. Chem.* 266:10754–10761.

Büllesbach, et al., 1980, "Human Proinsulin. VIII. Studies on the S–Tritylation of Reduced Proinsulin, Insulin A and B Chains and their Detritylation", *Hoppe Seyler's Z. Physiol. Chem.* 361:865–873.

Burkhardt, et al., 1994, "Structural Organization of the porcine and human genes Coding for a Leydig Cell–Specific Insulin–like Peptide (LEY I–L) and Chromosomal Localization of the Human Gene", *Genomics* 20:13–19.

Eddie et al., 1986, "Radioimmunoassay of Relaxin in Pregnancy with an Analogue of Human Relaxin", *Lancet* 1:1344–1346.

Eigenbrot, et al., 1991, "X–ray Structure of Human Relaxin at 1.5 A", *J. Mol. Biol.* 221:15–21.

Ellman, 1959, "Tissue Sulfhydryl Groups" *Arch. Biochem. Biophys.* 82:70–77.

Hock and Hollenberg, 1980, "Characterization of the Receptor for Epidermal Growth Factor–Urogastrone in Human Placenta Membranes", *J. biol. Chem.* 255:10731–10736.

Linde, et al., 1986, "Preparative Reversed–Phase High–Performance Liquid Chromatography of Iodinated Insulin Retaining Full Biological Activity", *J. Chromatogr.* 369:327–339.

Loumaye et al., 1978, "Characterization of Relaxin Radioimmunoassay Using Bolton–Hunter Reagent, First Results in Plasma during Pregnancy, and in Placenta, Corpora lutea and Ovarian Cysts in Woman", *Gynecologic and Obsteric Investigation* 9:262–267.

Olefsky, et al., 1982, "Potentiation of Insulin Binding and Insuling Action by Purified Porcine Relaxin", *Ann. NY Acad. Sci.* 380:200–216.

Schwabe and Büllesbach, 1994, "Relaxin: structures, functions, promises, and nonevolution", *FASEB J.* 8:1152–1160.

Schwabe and Harmon, 1978, "A Comparative Circular Dichroism Study of Relaxin and Insulin", *Biochem. Biophys. Res. Commun.* 84:374–380.

Sherwood et al., 1980, "Development of a homologous Radioimmunoassay for Rat Relaxin", *Endocrinology* 107:691–698.

Sherwood and Crnekovic, 1979, "Radioimmunoassay of Relaxin Throughout Pregnancy and during Paturition in the Rat", *Endocrinology* 104:893–897.

Sieber, et al., 1977, "Totalsynthese von Humaninsulin. IV. Beschreibung der Endstufen" (Total synthesis of human insuling.IV. Description of the final steps. *Helv. Chim. Acta* 60:27–37.

Steinetz, et al., 1960, "Bioassay of Relaxin Using a Reference Standard: A Simple and Reliable Method Utilizing Direct Measurement of Interpubic Ligament Formation in Mice" *Endocrinology* 67:102–115.

Tam, et al., 1991, "Disulfide Bond Formation in Peptides by Dimethyl Sulfoxide Scope and Applications", *J. Am. Chem. Soc.* 113:6657–6662.

Tashima, et al., 1995, "The Human Leydig Insulin–Like (hLEY 1–L) Gene is Expressed in teh Corpus Luteum and Trophoblast", *J. Clin. Endocrinal. Metab.* 80:707–710.

Yang, et al., 1992, "Relaxin Receptors in Mice: Demonstration of Ligand Binding in Symphyseal Tissues and Uterine Membrane Fragments", *Endocrinology* 130:179–185.

*Primary Examiner*—Elizabeth C. Kemmerer
*Assistant Examiner*—David S. Romeo
*Attorney, Agent, or Firm*—Pennie & Edmonds LLP

[57] ABSTRACT

The present invention relates to a relaxin-like factor, its derivatives or analogs, and uses thereof. The present invention further relates to compositions comprising a relaxin-like factor, its derivatives or analogs, and relaxin wherein such composition exhibits an additive or synergistic effect.

2 Claims, 8 Drawing Sheets

RELAXIN-LIKE FACTOR AND METHODS AND USES THEREOF

A portion of the work set forth herein was supported by grants NIHGMS-48893 and NSF MCB-9406656 and by the Medical University of South Carolina.

1. INTRODUCTION

The present invention relates to a relaxin-like factor, its derivatives or analogs, and uses thereof. The present invention further relates to compositions and formulations comprising a relaxin-like factor, its derivatives or analogs, and relaxin wherein such composition exhibits an additive or synergistic effect.

2. BACKGROUND OF THE INVENTION

A family of hormones, comprising insulin, insulin-like growth factors (I and II), bombyxin, molluscan insulin-related peptide and relaxin, has been identified and designated as "insulin-related." Blundell and Humbel, 1980, Nature 287:781–787; Büllesbach and Schwabe, 1991, J. Biol. Chem. 266:10754–10761. The proteins comprising this family of hormones represents a group of polypeptides having homologous primary and secondary structure but divergent biological functions.

Relaxin has been purified from a variety of species including porcine, murine, equine, shark, tiger, rat, dogfish and human. In the human, relaxin is most abundantly found in the corpora lutea (CL) of pregnancy. Mature human relaxin is a hormonal peptide of approximately 6000 daltons which facilitates the birth process by remodelling the reproductive tract before parturition. More specifically, relaxin appears to mediate the restructuring of connective tissues in target organs to obtain the required changes in organ structure during pregnancy and parturition. See, Hisaw, 1926, Proc. Soc. Exp. Biol. Med. 23:661–663; Schwabe, et al., 1977, Biochem. Biophys. Res. Comm. 75:503–570; James, et al., 1977, Nature, 267:544–546. A concise review of relaxin was provided by Sherwood, D. in The Physiology of Reproduction, Chapter 16, "Relaxin", Knobil, E. and Neill, J., et al. (eds.), (Raven Press Ltd., New York), pp. 585–673 (1988).

While predominantly a hormone of pregnancy, relaxin has also been detected in the non-pregnant female as well as in the male. Bryant-Greenwood, 1982, Endocrine Reviews 3:62–90; Weiss, 1984, Ann. Rev. Physiol. 46:43–52.

Two human gene forms encoding for human relaxin have been identified, (H1) and (H2). Hudson, et al., 1983, Nature 301 628–631; Hudson, et al., 1984, EMBO J., 3:2333–2339; and U.S. Pat. Nos. 4,758,516 and 4,871,670. Only one of the gene forms (H2) has been found to be transcribed in CL. It remains unclear whether the (H1) form is expressed at another tissue site, or whether it represents a pseudo-gene. When synthetic human relaxin (H2) and certain human relaxin analogs were tested for biological activity, the tests revealed a relaxin core necessary for biological activity as well as certain amino acid substitutions for methionine that did not affect biological activity. Johnston, et al., in Peptides: Structure and Function, Proc. Ninth American Peptide Symposium, Deber, C. M., et al. (eds.) (Pierce Chem. Co. 1985).

Methods of making relaxin are described in U.S. Pat. No. 4,835,251 and in co-pending U.S. Pat. No. 5,464,756 (PCT US90/02085) and PCT US94/06997. Methods of using relaxin in cardiovascular therapy and in the treatment of neurodegenerative diseases are described in U.S. Pat. No. 5,166,191 and in PCT US92/06927. Certain formulations of human relaxin are described in allowed U.S. Pat. No. 5,451,572.

The structure and biological function and activity of the remaining members of the insulin-related family have been extensively studied. See, e.g. Robinson and Fritz, 1981, Biol. Reprod. 24:1032–1041; Soder, et al., 1992, Endocrinology 131:2344–2350; Luthman, et al., 1989, Eur. J. Biochem 180(2):259–65; Jhoti, et al., 1987, FEBS Lett. 219:419–425; Smit, et al., 1988, Nature 331:535–538. Among the structural features shared between relaxin and the remaining members of the insulin-related family of hormones are molecular weight, a "two-chain" structure comprising a B-chain, a connecting C-peptide, and an A-chain, and the number and disposition of disulfide links.

Despite these similarities, the proteins comprising the insulin-related family have been found to have distinct biological functions and activities. It has been reported that this distinction is in large part a consequence of differences between a few type-specific amino acid residues. For example, the difference between the glycine in position A14 of human type II relaxin and the isoleucine in the equivalent position (A10) of insulin is considered critical in distinguishing between the biological activity of the two proteins. Schwabe and Büllesbach, 1994, FASEB J. 8:1–2.

A protein having the structural characteristics of insulin, insulin-like growth factor (IGF) and relaxin has been isolated recently from Leydig cells of the testes. Burkhardt, et al., 1993, Genomics 20:13–19. This protein, designated as a Leydig cell-specific insulin-like peptide (Ley I-L), has been characterized as being "insulin-like" due to the genomic location of the gene encoding Ley I-L vis a vis the gene encoding insulin (as compared to the genomic location of the gene encoding either relaxin or IGF). Burkhardt, et al., 1993, Genomics 20:13–19.

The Ley I-L protein has been characterized also as insulin-like, rather than either IGF-like or relaxin-like, based upon the protein's C-peptide chain length. More specifically, the C-peptide length of the Ley I-L protein is 49 amino acids, as compared to the 35 amino acid length of proinsulin C-peptide, the twelve amino acid length of the known proIGF C-peptides and the over one-hundred amino acid C-peptide length of prorelaxin. Finally, Ley I-L has been designated insulin-like based on the observation that the protein is expressed exclusively in prenatal and postnatal testicular Leydig cells. Burkhardt, et al., supra.

On the basis of the protein's similarities to insulin and the source of such protein, it was reported that the Ley I-L protein is implicated in testicular function. Id., Adham, et al., 1993, J. Rio. Chem. 268(35) :26668–6672.

In consultation with the inventors of the present invention, Tashima, et al., 1995, J. Clin. Endocrinal. Metab. 80:707–710, have investigated the accuracy of previous reports providing that the Ley I-L gene was only expressed in Leydig cells. Specifically, Tashima, et al. investigated whether the Ley I-L gene was present and expressed in female reproductive tissues, the human corpus luteum, trophoblasts, fetal membranes and breast tissue. As with the case with H2 relaxin, Tashima, et al. determined that the Ley I-L protein can be found in human corpus luteum and trophoblast. Unlike H2 relaxin, however, Ley I-L was not found to be expressed in fetal membranes, decidua and breast tissue.

Neither the Burkhardt/Adham group nor the Tashima group have reported the biological function of the Ley I-L protein. Thus, while the structure of this putative Ley I-L protein has been identified, no correct activity or use was known for this protein until the present invention, which completed the discovery of RLF through the identification and proof of its utility.

3. SUMMARY OF THE INVENTION

The present invention is directed to synthesized or recombinant compositions derived from the deduced amino acid and nucleic acid sequences for human Ley I-L. In one embodiment of the present invention, the composition comprises the full-length amino acid sequence for relaxin-like factor (RLF). In another embodiment of the present invention, the composition comprises a RLF protein derivative wherein the protein is shortened at either or both its 3' and 5' ends of either or both the A- or B-chains. In one embodiment, the A chain may be as short as fifteen amino acids in length and the B chain may be as short as thirteen amino acids in length. In yet further embodiments of the present invention, the composition is radiolabelled or represents an analog of RLF having relaxin-like activity.

The present invention is further directed to the use of such compounds for the treatment of diseases and disorders which may be otherwise treated with relaxin, either alone, or in combination with relaxin or other relaxin-like agents, and formulations thereof. In one embodiment of the present invention, the diseases or disorders are related to the abnormal expression of collagen and/or fibronectin. More specifically, such diseases or disorders include scleroderma and rheumatoid arthritis. In another embodiment of the present invention, the diseases and/or disorders are more generally related to the activation of one or more biological functions as a result of binding with the relaxin or RLF receptor. Such diseases and/or disorders may include cardiovascular disease, sinus bradycardia, neurodegenerative or neurologic disease, depression and hair loss.

The present invention is also related to the use of RLF, whether labelled or unlabelled, as a tracer which could then be used to separate, by HPLC, the different RLF derivatives to yield a carrier-free tracer, in binding assays, and for RLF receptor mapping.

4. DESCRIPTION OF THE DRAWINGS

FIG. 1. FIG. 1 depicts the primary structure of the relaxin-like factor, (SEQ IN NO:3 and SEQ ID NO:4) as compared with the sequences of human relaxin (SEQ ID NO:2 and SEQ ID NO:5) and insulin (SEQ ID NO:1 and SEQ ID NO:6) wherein the relative positions of the B-chain arginines in RLF, as compared to relaxin, is highlighted.

Figure 2:
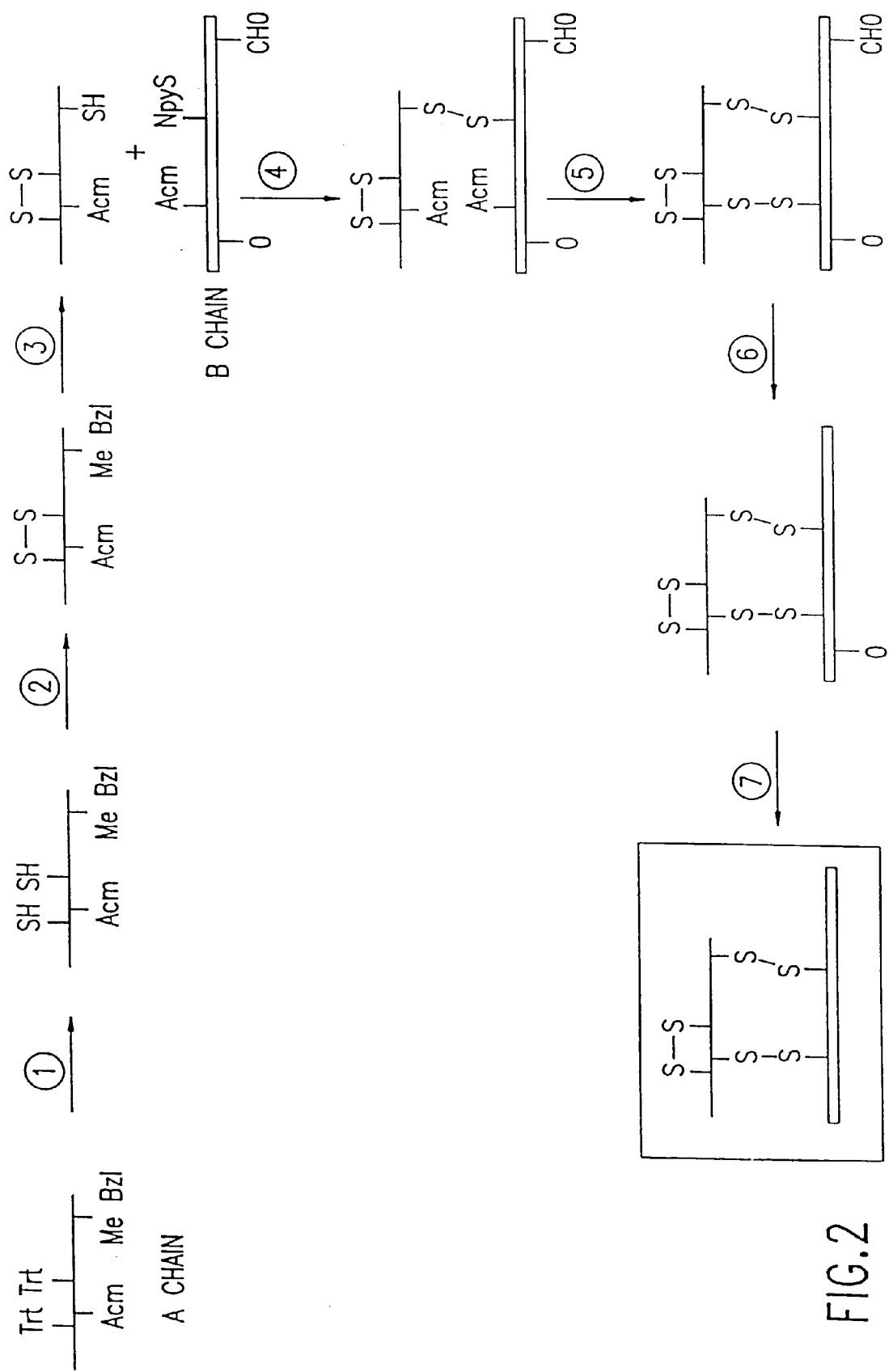

FIG. 2. FIG. 2 depicts a schematic of the site-directed sequential disulfide link formation. Specifically, the schematic provides information regarding: 1) trifluoroacetic acid (TFA) deprotection; 2) oxidation of the thiols using DMSO/50 mM $NH_4HCO_3$ (1:2 v/v); 3) HF-deprotection of Cys(4-methylbenzyl); 4) combination of A and B chain pH 4.5 in 8 M guanidinium chloride; 5) formation of the third disulfide link by reaction with iodine in 70% acetic acid; 6) liberation of the tryptophan side chain with 10% piperidine; 7) reduction of methionine sulfoxide with a 33 fold excess of $NH_4I$ in 90% TFA.

Figure 3:
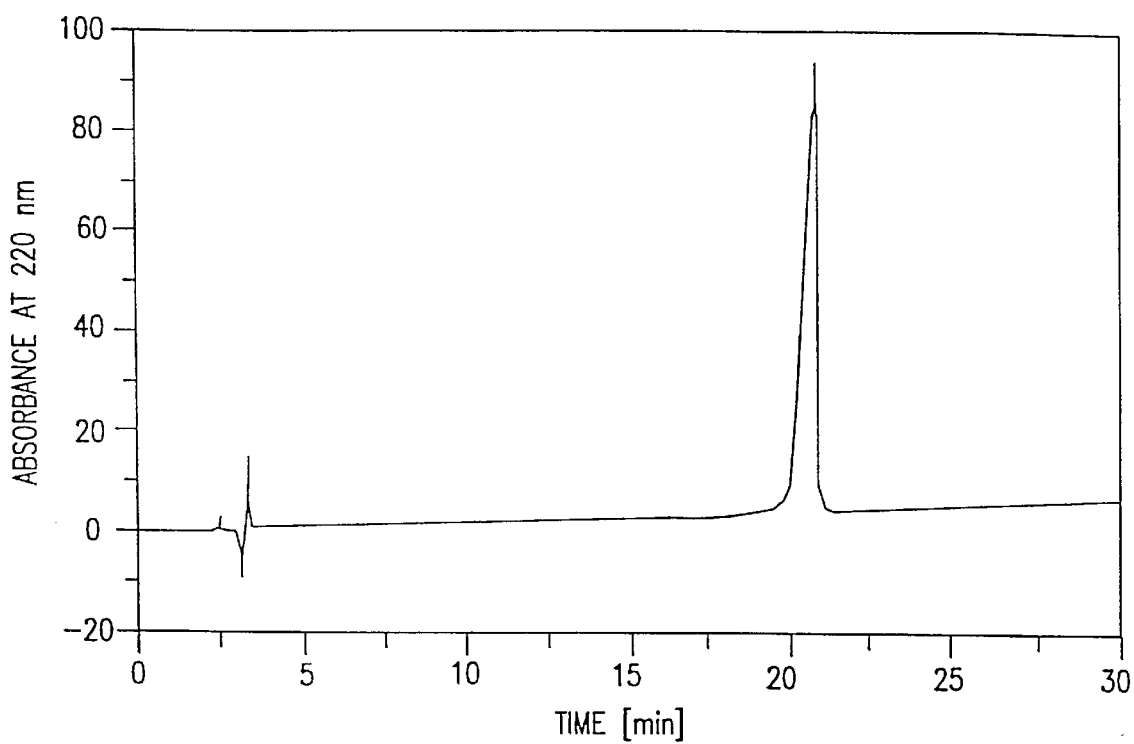

FIG. 3. FIG. 3 depicts the HPLC record of the purified RLF. Chromatography was performed on Synchropak RP-P (4.1×250 mm) using a linear gradient from 20–50% in 30 min (A:0.1% TFA in $H_2O$ and B:0.1% TFA in 80% acetonitrile) at a flow rate of 1 ml/min.

Figure 4:
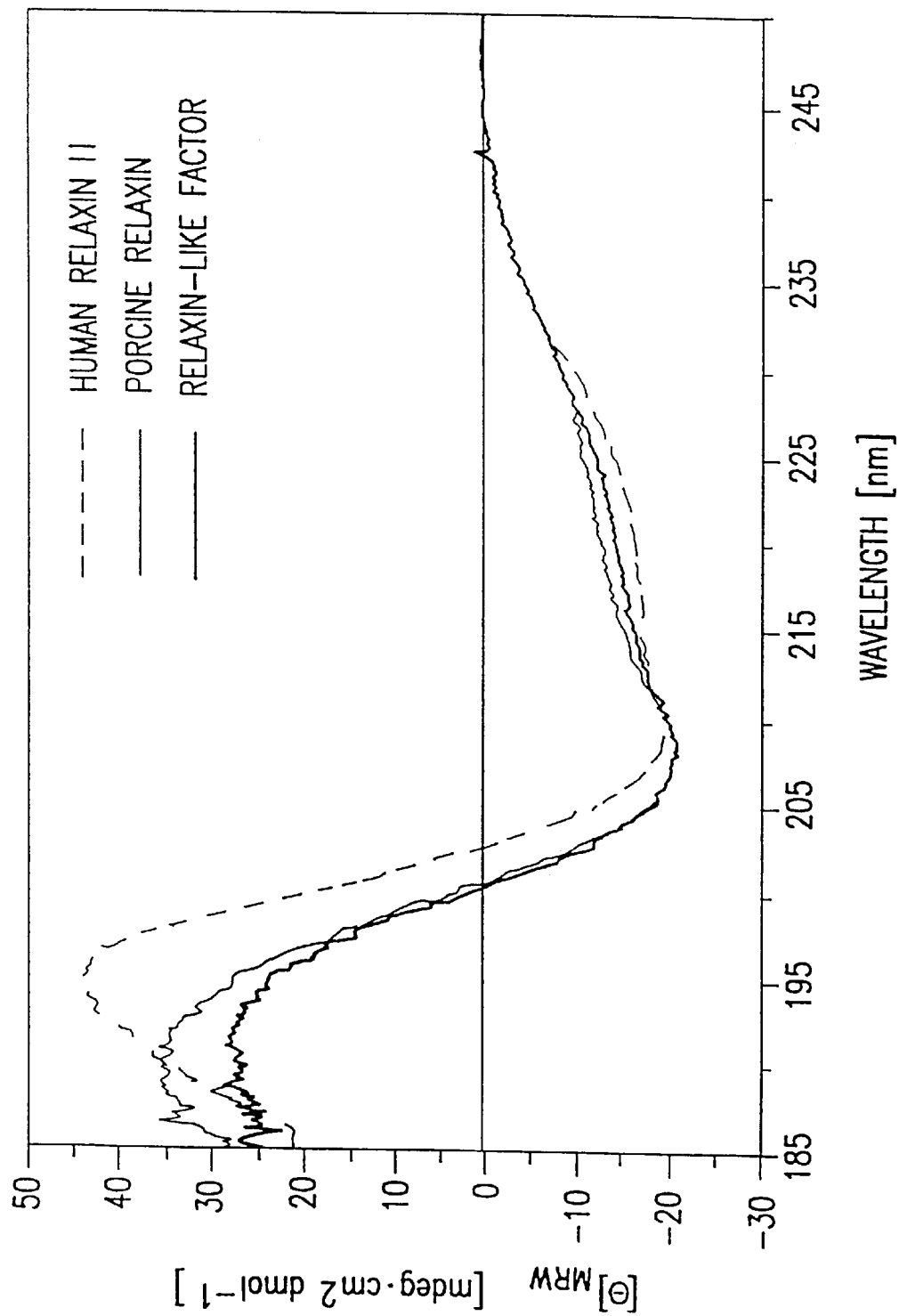

FIG. 4. FIG. 4 depicts a comparison of the CD spectra of human relaxin, human RLF, and porcine relaxin.

Figure 5:
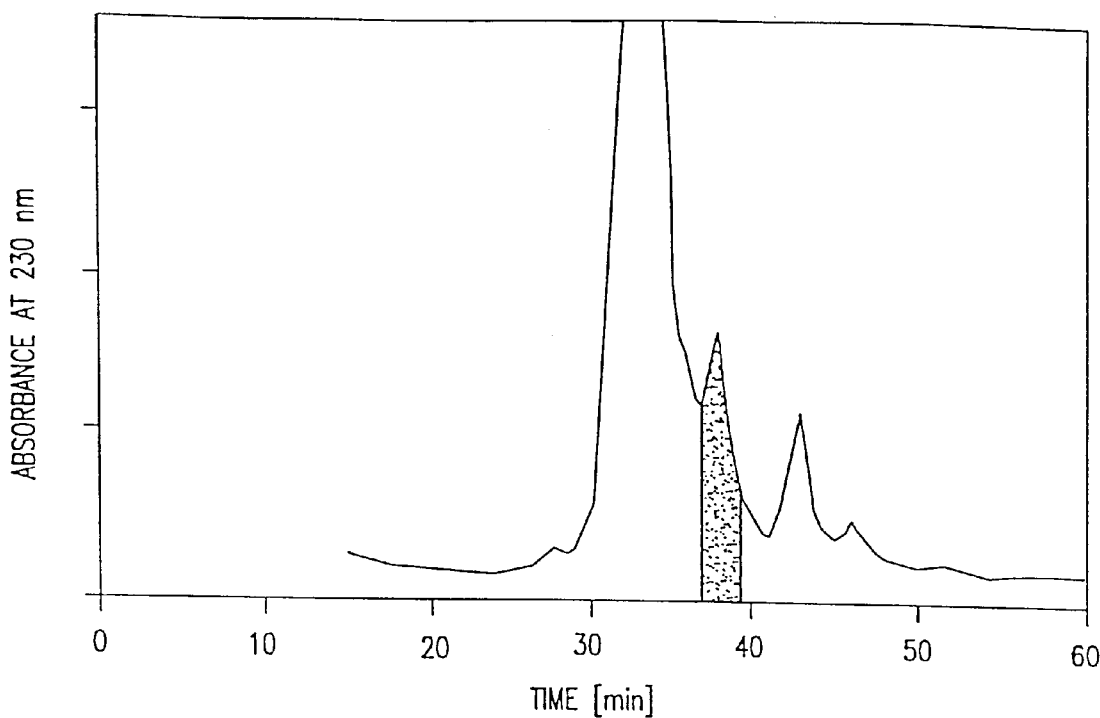

FIG. 5. FIG. 5 depicts the elution record of the HPLC separation of an RLF tracer preparation. The largest peak is unmodified RLF and the shaded region is the major radioactive peak used as tracer. Chromatography was performed on Aquapore 300 (2.1 mm×30 mm) using a linear gradient from 23% B to 34% B over 60 min (A: 0.1% TFA in $H_2O$ and B: 0.1% TFA in 80% acetonitrile) at a flow rate of 0.1 ml/min.

Figure 6:
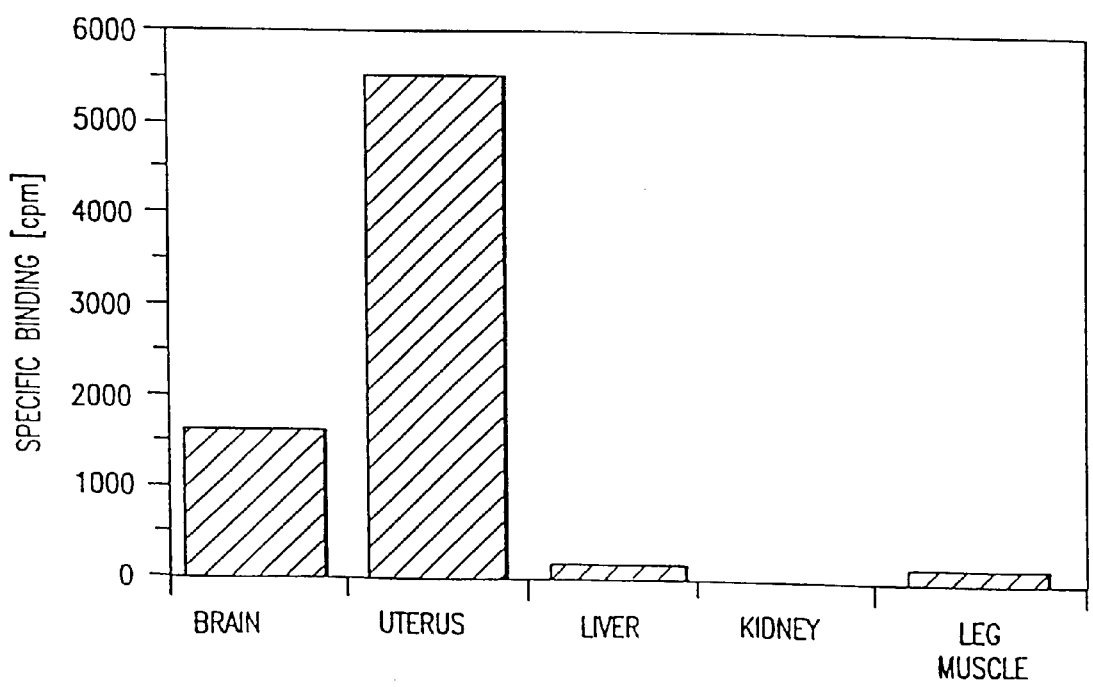

FIG. 6. FIG. 6 depicts the tissue distribution of RLF receptors in female estrogen primed mice as measured in vitro in a receptor-binding assay.

Figure 7:
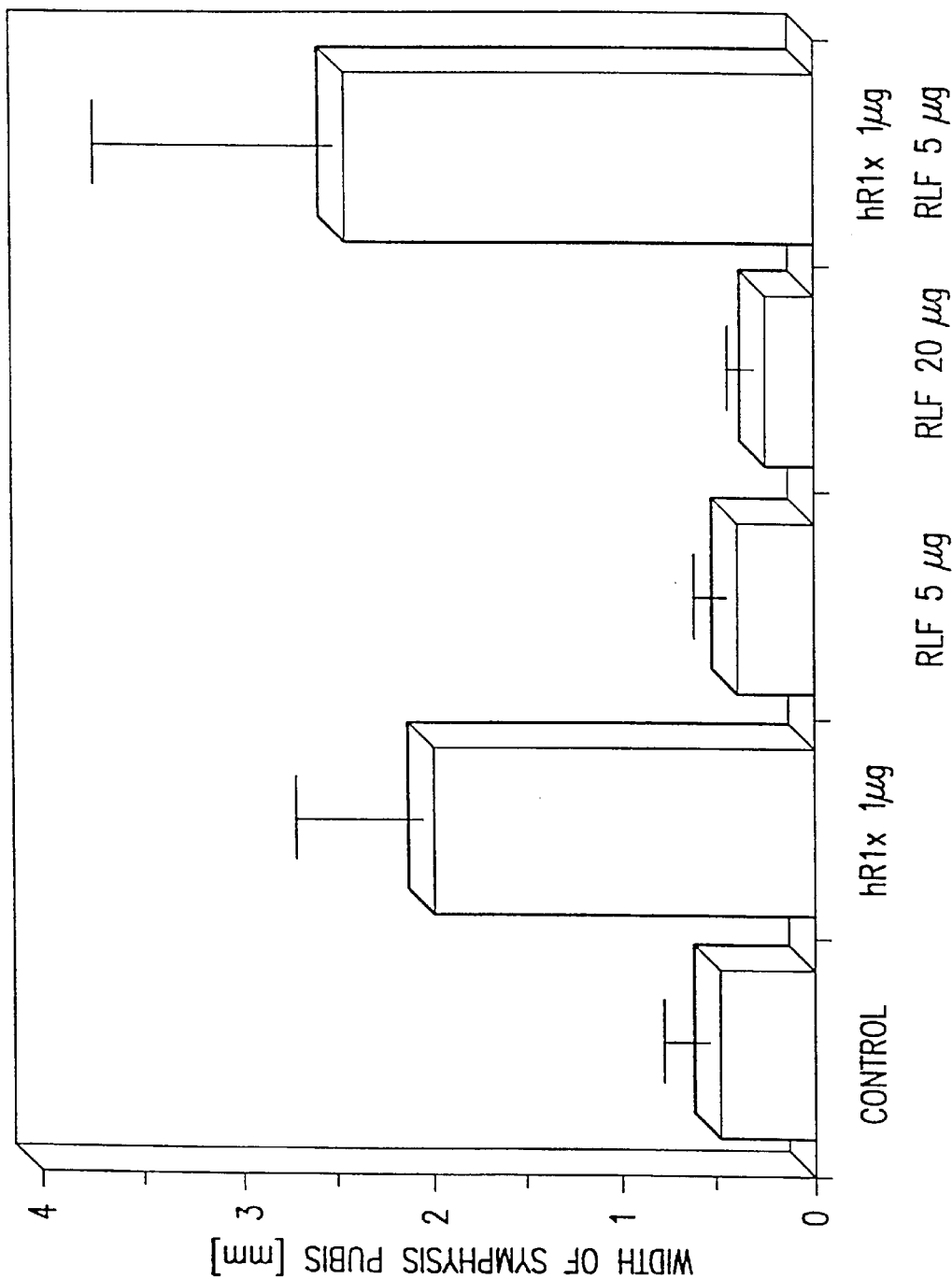

FIG. 7. FIG. 7 depicts the bioactivity of an increasing amount of relaxin in the presence and absence of 5 $\mu$g of RLF per animal. The increase in symphyseal width was easily recognized.

Figure 8:
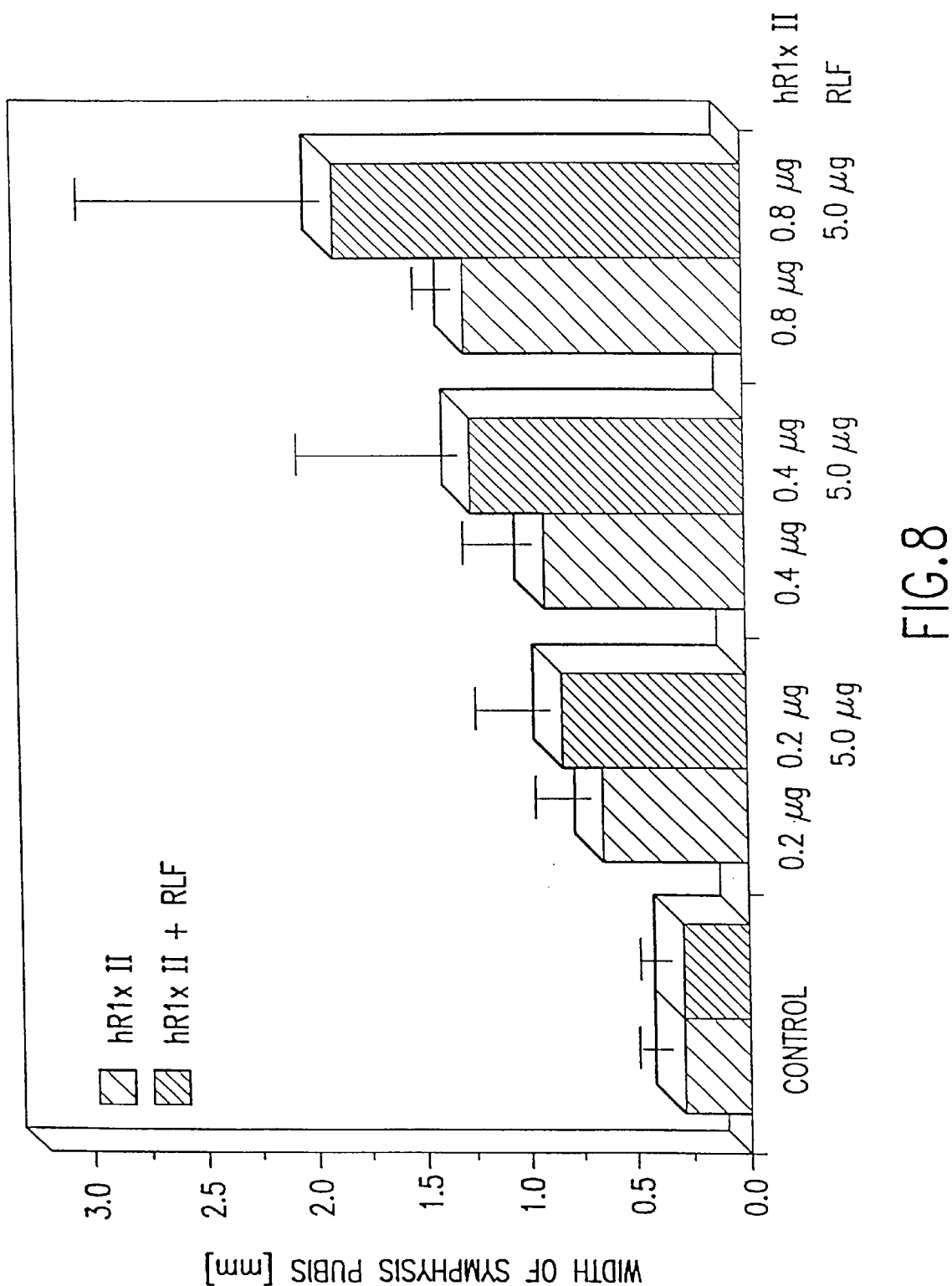

FIG. 8. FIG. 8 depicts the bioactivity of an increasing amount of RLF in the presence of a uniform amount of human relaxin again shows relaxin enhancement.

Figure 9:
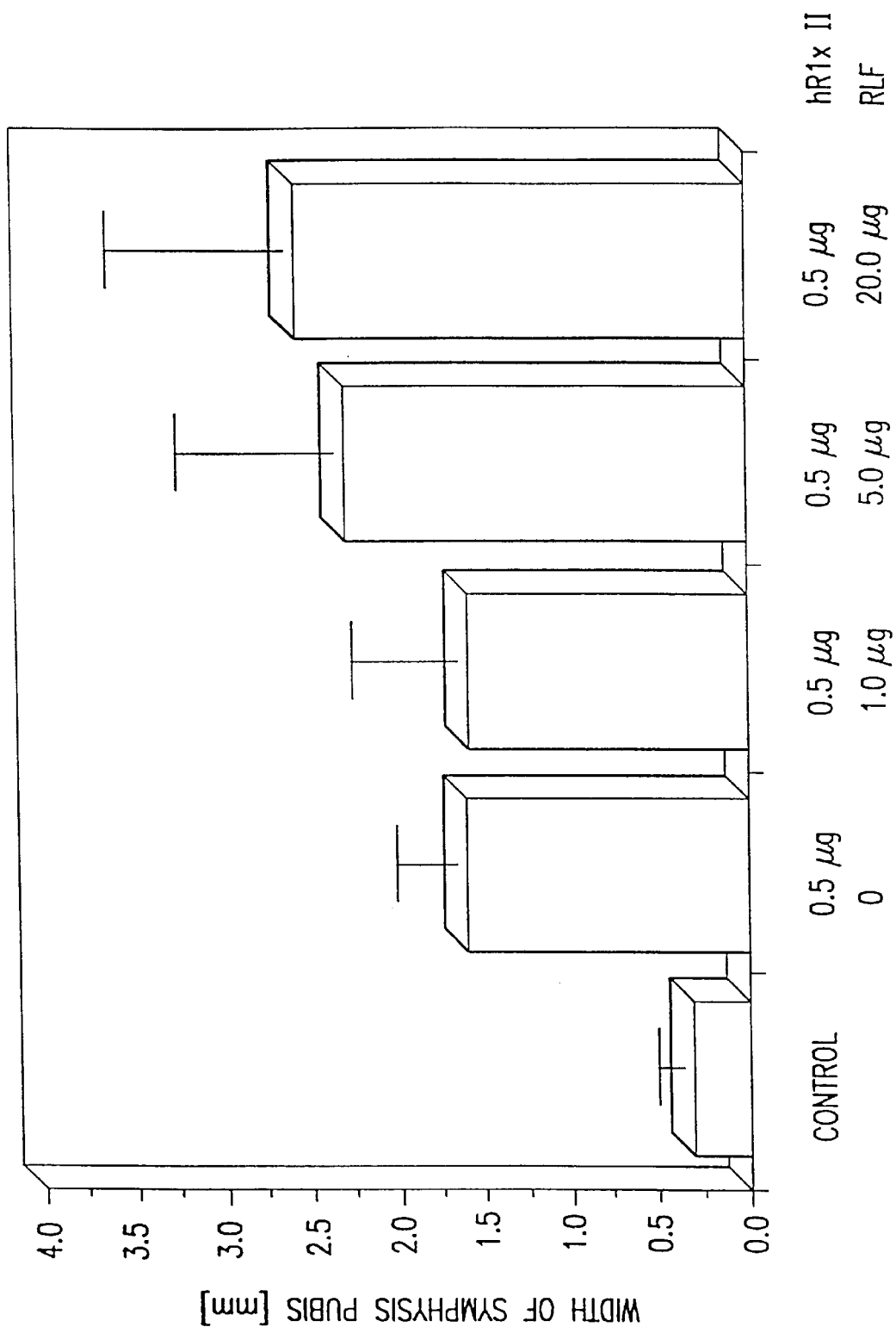

FIG. 9. FIG. 9 depicts a comparative bioassay of relaxin, RLF, and an optimal dose of both. RLF alone does not cause symphyseal widening but the high dose of the mixture still improves upon the high dose of relaxin alone.

5. DETAILED DESCRIPTION OF THE INVENTION

5.1. Definitions

As used in the present specification, the following words and phrases are generally intended to have the meanings as set forth below, except to the extent that the context in which they are used indicates otherwise.

"Optional" or "optionally" means that the subsequently described event or circumstance may or may not occur, and that the description includes instances where said event or circumstance occurs and instances in which it does not.

The term "effective amount" means a dosage sufficient to provide treatment for the disease state being treated. This will vary depending on the patient, the disease and the treatment being effected.

The term "relaxin" means human relaxin, including full length relaxin or a portion of the relaxin molecule that retains biological activity [as described in U.S. Pat. No. 5,023,321, preferably recombinant human relaxin (H2)] and other active agents with relaxin-like activity, such as agents that competitively displace bound relaxin from a receptor. Relaxin can be made by any method known to those skilled in the art, preferably as described in U.S. Pat. No. 4,835,251 and in co-pending U.S. Pat. No. 5,464,756 (PCT US90/02085) and PCT US94/06997.

5.2. Relaxin-Like Factor: Structure And Activity

RLF shares primary and secondary structural homology with relaxin, insulin and the other members of the insulin-related family of hormones. As reported previously, RLF is structurally closer to insulin than relaxin. The deduced primary structure of RLF is set forth at FIG. 1 SEQ ID NOS:3 and 4.

Contrary to early reports, however, the biological function and activity of RLF is similar to relaxin and distinct from insulin. For example, notwithstanding the shift in amino acid sequence of the receptor interacting region between RLF and relaxin, RLF interacts with the mouse brain receptor to which relaxin binds.

A basis for the present invention is the inventors' unexpected discovery that the previously isolated but uncharacterized RLF protein binds specifically to crude membrane preparations of mouse uterus and brain and shows crossreactivity with the relaxin receptor, but not the insulin receptor.

The deduced amino acid sequence for RLF would have predicted an opposite result because the critical two Arg residues separated by three amino acids sequence in RLF is offset toward the C-terminal end of the B chain by exactly one turn of the helix. Thus, although RLF projects the arginines at nearly right angles away from the molecular surface in the manner of relaxin, one would expect that shifting the whole receptor-binding site would present quite a different binding environment to the receptor.

Notably, although RLF binds to the relaxin receptor, it does not appear to competitively bind to the relaxin receptor, vis a vis relaxin, except at higher concentrations. Rather, RLF appears to stimulate relaxin response. Thus, RLF can play an important supportive role for the relaxin action in humans. In addition, preliminary experiments suggest that RLF plays a role independent of relaxin in the male gonads.

In addition, although relaxin-like activity has historically been considered in terms of softening the pubic and cervical ligaments in preparation for parturition, it has also been shown to directly effect cells outside of the reproductive system. For example, consistent with relaxin, RLF may also be instrumental in inhibiting collagen and/or fibronectin overexpression and diseases related thereto (e.g. scleroderma)

Moreover, although RLF possesses relaxin-enhancing properties, as described herein, RLF possess independent and potentially additional biological activity.

5.3. RLF Derivatives And Analogs

Following the present identification of RLF as a protein having relaxin-like (rather than insulin-like) activity, to the extent that RLF shares primary and secondary homology to relaxin, as well as insulin, identification of biologically active derivatives and analogs of relaxin evidences the identity of biologically active RLF derivatives and analogs. Active relaxin analogs and derivatives have been identified to include, for example, shortening either or both the 5' and 3' end of the protein. See e.g., U.S. Pat. No. 5,023,321. The present invention is therefore directed to biologically active RLF derivatives wherein the 5' and/or 3' end of the protein has been shortened. See, above referenced patents.

Importantly, it has been observed in human relaxin that the arginines at positions B13 and B17 and potentially the amino acids of the first helix turn in the midregion of the B-chain (Arg-Glu-Leu-Val-Arg) (amino acid residues 13 to 17 of SEQ ID NO:5) are necessary or important to relaxin activity. Other RLF analogs and derivatives may be obtained using known techniques and this structural information regarding relaxin.

Whether the RLF derivative or analog possesses relaxin-like activity and/or utility may be determined using assays known in the art for detecting relaxin activity. For example, bioassays used for the measurement of active relaxin during pregnancy and non-pregnancy, as described in Steinetz et al., 1960, *Endocrinology* 67:102–115 and Sarosi et al., 1983, *American Journal of Obstetrics and Gynecology* 145:402405, may be used.

Similarly, specific immunoassays to detect for the presence of proteins having relaxin-like activity may also be used. See e.g., Sherwood et al., 1975, *Endocrinology* 107:691–696; O'Bryne and Steinetz, 1976, *Proceedings of the Society for Experimental Biology and Medicine* 152:272–276. The presence and activity of synthetic analogs of human relaxin comprising one or more accessible tyrosines (permitting direct iodination) may also be tested using a radioimmunoassay (RIA). Eddie et al., 1986, *Lancet* 1:1344–1346.

Each of the above-described assays, however, are limited in their application. Thus, as set forth below and as described in more detail in a co-pending application, filed concurrently herewith and entitled "Relaxin Diagnostic Assays And Kits," additional assays may also be used to assay RLF to determine the protein's activity and preferred applications.

5.4. Production Of RLF

RLF may be produced using techniques previously disclosed as useful in producing relaxin and insulin. For example, the cDNA for RLF disclosed in Burkhardt, et al., 1994, *Genomics* 20:13–19 and Adham, et al., 1994, *J. Biol. Chem.* 268:26668–26672 may be used to recombinantly produce RLF according to processes previously described as useful in recombinantly manufacturing relaxin (e.g., U.S. Pat. Nos. 4,758,516, 4,871,670, 4,835,251 and co-pending U.S. Pat. No. 5,464,756 (PCT US90/02085) and PCT US94/06997). Similarly, such sequence information may be used to synthesize RLF according to the methods of Büllesbach and Schwabe, 1991, *J. Biol. Chem.* 266:10754–10761, for synthesizing relaxin.

Derivatives and analogs of RLF also may be synthesized according to the methods of Büllesbach and Schwabe, supra. Alternatively, such derivatives and analogs may be produced recombinantly using, for example, site directed mutagenesis techniques as set forth in Tsurushita, et al., 1988, *Gene* 62:135–139.

Relaxin, for use in compositions containing RLF, may be obtained using any number of readily available techniques.

For example, naturally-occurring relaxin may be purified from a variety of species including porcine, murine, equine, shark, tiger, rat, dogfish and human. In the human, relaxin is found in most abundance in the corpora lutea (CL) of pregnancy.

Relaxin may also be synthesized according to the techniques described above, with respect to RLF, or alternatively, recombinantly, by relying upon the disclosed nucleic acid sequences and deduced amino acid sequences for relaxin. In humans, two gene forms encoding for human relaxin have been identified, (H1) and (H2) and their use to recombinantly manufacture relaxin, and preferably relaxin (H2), have been described. Hudson, et al., 1983, *Nature* 301 628–631; Hudson, et al., 1984, *EMBO J.*, 3:2333–2339; and U.S. Pat. Nos. 4,758,516 and 4,871,670. Methods of making relaxin are also described in U.S. Pat. No. 4,835,251 and in co-pending U.S. Pat. No. 5,464,756 (PCT US90/02085) and PCT US94/06997.

Notably, when synthetic human relaxin (H2) and certain human relaxin analogs were tested for biological activity, the tests revealed a relaxin core necessary for biological activity as well as certain amino acid substitutions for methionine that did not affect biological activity. Johnston, et al., in *Peptides: Structure and Function, Proc. Ninth American Peptide Symposium*, Deber, C. M., et al. (eds.) (Pierce Chem. Co. 1985).

5.5. Indications/Methods Of Use

In vitro, proteins having relaxin-like activity decrease collagen synthesis by human dermal and synovial fibroblasts upregulated to overexpress collagen with transforming growth factor-beta (TGF-beta) or interleukin-1, and by fibroblasts constitutively overexpressing collagen obtained from scleroderma patients. For example, relaxin decreases collagen accumulation in vivo in two rodent models of fibrosis. Relaxin or relaxin-like proteins also increase the secretion of the collagenolytic metalloproteinase, collagenase, and also down-regulates the expression of the metalloproteinase inhibitor, tissue inhibitor of metalloproteinases.

Relaxin has been implicated consequently in the treatment and diagnosis of various diseases and disorders. For example, studies provide evidence that relaxin is effective in the treatment of scleroderma, sinus bradycardia, cardiovascular disease, neurodegenerative and neurologic disorders, hair loss, depression. See e.g., U.S. Pat. No. 5,166,191; PCT US92/06927; U.S. Ser. No. 08/483,476, filed concurrently herewith. Evidence also suggests allowed the use of relaxin in diseases and disorders related to the abnormal expression of collagen or fibronectin, such as scleroderma or rheumatoid arthritis.

As provided herein, RLF possesses relaxin-like biological activity and is therefore similarly implicated in the above described diseases. Moreover, to the extent that RLF is also shown to enhance the activity of relaxin, RLF, as administered in combination with relaxin or another agent, is also indicated for the treatment of the above-identified diseases.

Additionally, as more fully discussed in the U.S. Application entitled "Relaxin Diagnostic Assays and Kits," filed concurrently herewith, filed Jun. 7, 1995, U.S. Ser. No. 08/488,399, diagnostic assays for determining the predisposition or presence of prostate, breast, testicular, ovarian and other cancers having common stem cell heritage, which rely on detecting the presence of relaxin may also be adjusted to rely upon the detection of RLF. Such assays can also be used to follow-up on tumor metastases after ablation of cancer.

5.6. Pharmaceutical Dosage Requirements, Formulations And Routes Of Administration The following dosage requirements, formulations and routes of administration for RLF are discussed below:

5.6.1. Effective Dosage.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the IC50 as determined in cell culture. Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1).

Dosage amount and interval may be adjusted individually to provide plasma levels of the active moiety which are sufficient to maintain the relaxin-like activity and effects.

Administration of RLF, with relain or other active agents, can be via any of the accepted modes of administration for agents that serve similar utilities, preferably by systemic administration.

While human dosage levels for treating many of the above-identified relaxin-related diseases or disorders have yet to be optimized for RLF, administered alone or in combination with relaxin, generally, a daily dose is from about 0.1 to 500.0 µg/kg of body weight per day, preferably about 6.0 to 200.0 µg/kg, and most preferably about 12.0 to 100.0 µg/kg, depending on whether RLF is administered alone or in combination with relaxin. Generally it is sought to obtain a serum concentration of RLF, alone or in combination with relaxin, approximating or greater than normal circulating levels in pregnancy, i.e., 1.0 ng/ml, such as 1.0 to 20 ng/ml, preferably 1.0 to 20 ng/ml.

For administration to a 70 kg person, the dosage range would be about 7.0 µg to 3.5 mg per day, preferably about 42.0 µg to 2.1 mg per day, and most preferably about 84.0 to 700.0 µg per day. The amount of RLF administered will, of course, be dependent on the subject and the severity of the affliction, the manner and schedule of administration and the judgment of the prescribing physician. One treatment regimen can employ a higher initial dosage level (e.g., 100 to 200 µg/kg/day) followed by decreasing dosages to achieve steady relaxin or relaxin-like serum concentration of about 1.0 ng/ml. Another treatment regimen, particularly postpartum depression, entails administration of an amount of relaxin sufficient to attain normal pregnancy levels of relaxin (about 1.0 ng/ml) followed by gradual decreasing dosages until relaxin serum levels are no longer detectable (e.g. less than about 20 picograms/ml), optionally discontinuing treatment upon reaching that dosage level.

In employing RLF, either alone or in combination with relaxin, for treatment of the above conditions, any pharmaceutically acceptable mode of administration can be used. RLF can be administered either alone or in combination with other pharmaceutically acceptable excipients, including solid, semi-solid, liquid or aerosol dosage forms, such as, for example, tablets, capsules, powders, liquids, gels, suspensions, suppositories, aerosols or the like. Relaxin can also be administered in sustained or controlled release dosage forms (e.g., employing a slow release bioerodable delivery system), including depot injections, osmotic pumps (such as the Alzet implant made by Alza), pills, transdermal (including electrotransport) patches, and the like, for prolonged administration at a predetermined rate, preferably in unit dosage forms suitable for single administration of precise dosages. The compositions will typically include a conventional pharmaceutical carrier or excipient and RLF. In addition, these compositions may include other active agents, carriers, adjuvants, etc.

In a preferred aspect of the invention, a sustained/controlled release RLF formulation was a selectively permeable outer barrier with a drug dispensing opening, and an inner RLF-containing portion designed to deliver dosage of RLF progressively diminished as a predetermined rate (e.g. containing about 30 mg of RLF in a matrix for delivery of initially about 500 µg per day diminishing as a rate of 10 µg per day.

In another preferred aspect of the invention, a sustained/controlled release RLF formulation has a selectively permeable outer barrier with a drug dispensing opening, a first inner relaxin-containing portion designed for steady state release of relaxin at a therapeutically effective daily dosage (e.g. containing about 50 mg of relaxin in a matrix for continuous delivery of about 500 μg per day), and a second inner RLF-containing portion designed to deliver a dosage of RLF progressively diminishing at a predetermined rate (e.g. containing about 3 mg of relaxin in a matrix for delivery of initially about 500 μg per day diminishing at a rate of 50 μg per day) commencing upon exhaustion of the relaxin from the first inner portion.

Generally, depending on the intended mode of administration, the pharmaceutically acceptable composition will contain about 0.1% to 90%, preferably about 0.5% to 50%, by weight of RLF, either alone or in combination with relaxin, the remainder being suitable pharmaceutical excipients, carriers, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The formulations of human relaxin described in U.S. Ser. No. 08/050,745 are particularly preferred.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

5.6.2. Routes Of Administration.

Suitable routes of administration may, for example, include oral, rectal, transmucosal, or intestinal administration. Parenteral administration is generally characterized by injection, either subcutaneously, intradermally, intramuscularly or intravenously, preferably subcutaneously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, and the like.

The percentage of RLF and/or relaxin contained in such parenteral compositions is highly dependent on the specific nature thereof, as well as the needs of the subject. However, percentages of active ingredient of 0.01% to 10% in solution are employable, and will be higher if the composition is a solid which will be subsequently diluted to the above percentages. Preferably the composition will comprise 0.2–2% of the RLF, alone or in combination with relaxin in solution.

A more recently devised approach for parenteral administration employs the implantation of a slow-release or sustained-release system, such that a constant level of dosage is maintained. See, e.g., U.S. Pat. No. 3,710,795.

Alternately, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tissue-specific antibody. The liposomes will be targeted to and taken up selectively by the tissue.

5.6.3. Composition/Formulation.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Formulations of RLF may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients. In such a case, the particles of the formulation may advantageously have diameters of less than 50 microns, preferably less than 10 microns. See, e.g., U.S. Pat. No. 5,364,838, which discloses a method of administration for insulin that can be adapted for the administration of RLF, alone or in combination with relaxin in the present invention.

RLF for treatment of such disorders such as alopecia, may also be administered topically in a formulation adapted for application to the scalp, such as a shampoo (e.g., as disclosed in U.S. Pat. No. 4,938,953, adapted according to methods known by those skilled in the art, as necessary for the inclusion of protein ingredients) or a gel (e.g., as disclosed in allowed U.S. Pat. No. 5,451,572) optionally with increased relaxin concentrations to facilitate absorption.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

5.6.4. Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of depression, sinus bradycardia, hair loss, neurologic or neurodegenerative diseases, scleroderma, cardiovascular disease or disorders or diseases related to uncontrolled or abnormal collagen or fibronectin formation.

More specific dosage, formulation and methods of administration may be derived from information contained in U.S. Pat. No. 5,166,191, PCT US92/06927 and U.S. Pat. No. 5,451,572, and co-pending application U.S. Ser. No. 08/483, 476, allowed, filed concurrently herewith.

6. EXAMPLES

The following preparations and examples are given to enable those skilled in the art to more clearly understand and to practice the present invention. They should not be considered as limiting the scope of the invention, but merely as being illustrative and representative thereof.

6.1. RLF Synthesis And Confirmation Of Synthesized Protein

As described above, RLF may be produced by isolating the protein from natural sources, synthesizing the protein based on RLF's deduced amino acid sequence and recombinantly manufacturing the protein based upon available cDNA data.

One procedure for synthesizing RLF is as follows:

Materials. L-Amino acid derivatives for peptide synthesis were purchased either from Bachem Bioscience (Philadelphia, Pa.) or Bachem California (Torrance, Calif.). Solvents for peptide synthesis and chromatography were distilled in glass (Burdick and Jackson; Muscagon, Mich.), and the chemicals for peptide synthesis were obtained from Perkin Elmer Applied Biosystems (Foster City, Calif.). Other chemicals of analytical grade were used without further purification.

Methods. The following method was followed to synthesize RLF:

Peptide Synthesis: The B chain of the RLF protein was synthesized by tert butyloxycarbonyl[1]-chemistry using conventional HF-labile side chain-protecting groups for all three functional amino acids except cysteines. Cysteine B10 was protected by the acetamidomethyl group and B23 by the thiol-protecting/activating group [S-(3-nitro-2-pyridinesulfenyl)] (CysB23). Methionine was protected by sulfoxide formation, and tryptophan by the N(in)formyl group. The synthesis was performed on an Applied Biosystems peptide synthesizer model 430A on [4-(oxymethylphenylacetamidomethyl] resin loaded with 0.4 mmol tert butyloxycarbonyl-alanine. Deprotection and removal from the solid support was accomplished by HF-treatment in the presence of 5% m-cresol. The crude peptide was extracted with 20% acetic acid and lyophilized (yield 1.387 g). The B chain was purified on Sephadex G50-sf (2.5 cm×50 cm) in 1 M acetic acid (yield:840 mg), followed by preparative HPLC on Synchropak RP-P (2.1 cm×25 cm) in portions of 50 to 70 mg. The mobile phase consisted of 0.1% trifluoroacetic acid (TFA) in water (solvent A) and 0.1% TFA in 80% acetonitrile (solvent B). The column was equilibrated in 20% B and the peptide eluted with a linear gradient of 20% B to 50% B over 1 h at a flow rate of 5 ml/min (overall yield:233 mg). Amino acid composition: Thr 2.00 (2); Ser 0.86 (1); Glu 2.90 (3); Gly 3.28 (3); Ala 2.16 (2); Cys 0.89 (2); Val 3.19 (3); Met 1.22 (1); Leu 1.94 (2); Phe 0.99 (1); His 2.44 (2); Lys 0.96 (1); Arg 3.81 (4).

The A chain (0.25 mmol) was synthesized via Fast-moc chemistry on an ABI peptide synthesizer (model 430A) on p-benzyloxybenzyl resin. All side chains were protected by TFA-abile protecting groups except Cys(A11), which was acetamidomethyl-protected, and Cys (A24) which was protected by the HF-labile p-menthylbenzyl group. The A chain was deprotected with TFA/thiophenol (10:1 v/v), using 50 mg peptidyl resin/ml for 90 min at room temperature (5). The TFA was evaporated and the peptide precipitated with ether. The precipitate was collected by centrifugation, the supernatant discarded, and the pellet washed twice with ether and air-dried. The peptide was suspended in water, dissolved by the addition of ammonia, and desalted on Sephadex G25-m in 50 mM $NH_4HCO_3$. To the eluate (100 ml) 50 ml of $Me_2SO$ was added in order to accelerate the oxidation of the intrachain disulfide bond A10–A15 (6). The progress of oxidation was observed by the Ellman reaction (7). After completion of the disulfide bond formation the A chain was dialyzed against water and lyophilized (yield 372.3 mg). Aliquots of 20 mg were further purified by preparative HPLC on Synchropak RP-P (10 mm×250 mm), using 0.1% TFA in water for solvent A and 0.1% TFA in 80% acetonitrile for solvent B. The column was equilibrated in 30% B and the peptide eluted with a linear gradient of 30% B to 50% B over 30 min at a flow rate of 3 ml/min (overall yield: 166.5 mg). Amino acid composition: Asp 2.20 (2); Thr 3.00 (3); Ser 0.99 (1); Glu 1.92 (2); Pro 2.25 (2); Gly 1.06 (1); Ala 4.18 (4); Cys 1.62 (4); Leu 3.60 (4); Tyr 1.82 (2); Arg 0.98 (1).

For chain combination, 33.4 mg (11.3 μmol) of the A chain(acetamidomethylA10, 4-methylbenzylA24) was treated with 4 ml of HF in the presence of 200 μl of m-cresol for 45 min at 0° C. Thereafter the HF was evaporated in a stream of nitrogen and the peptide precipitated with ether. The pellet was collected and dried over KOH in vacuo for 30 min. The monothiol A chain was dissolved in 4 ml of 8 M guanidiniumchloride in 0.1 M acetic acid at pH 4.5 and added to 36.3 mg (9.6 μmol) of the B chain. The disulfide bond A24/B23 was formed at 37° C. for 24 h and the resulting product separated first onSephadex G50-sf in 1 M acetic acid (column 2.5 cm×50 cm) (yield 48.7 mg, 78.3%), followed by preparative HPLC on Synchropak RP-P (10 mm×250 mm) using 0.1% TFA in water for solvent A and 0.1% TFA in 80% acetonitrile for solvent B. The column was equilibrated in 30% B and the peptide eluted with a linear gradient of 30% to 45% B over 30 min at a flow rate of 3 ml.min (yield: 34.1 mg, 54.8%).

The resulting peptide contained acetamidomethyl groups in positions Cys A11 and Cys B10, the N(in) formyl group in Trp B27, and a sulfoxide in the side chain of Met B5. For the formation of the third disulfide bond the peptide (9.3 mg) was dissolved in water (3.5 ml) and added to a stirred solution consisting of acetic acid (3.5 ml) 6 N HCl (19.1 μl) and 3 ml of 50 mM iodine in acetic acid (8). The reaction was performed at room temperature for 10 min, quenched with ascorbic acid, and the product was desalted on Sephadex G25-sf in 1 M acetic acid and lyophilized. After purification by preparative HPLC (conditions as before) (yield: 3.42 mg, 36.8%) the protein still contained protecting groups in Trp (B27) and Met (B5).

Complete deprotection was achieved first by treatment of 11.3 mg of the peptide with 2 ml of water/piperidine 9:1 (v/v) for 2 min at room temperature. The base was neutralized with 0.4 ml acetic acid and the peptide purified by preparastive HPLC, dried (yield:11.0 mg, 97.5%), and 10 mg of peptide-containing methionine sulfoxide was reduced with 1 ml of TFA/0.5 M $NH_4I$ in water 9:1 v/v for 15 min at )° C. Free iodine was reduced with 0.5 M ascorbic acid in water and the reaction quenched by dilution with water. The final peptide was recovered by preparative HPLC (conditions as before) (yield 7.57 mg=75.7%). Amino acid compositions: Asp 2.02 (2), Thr 4.79 (5), Ser 1.77 (2), Glu 4.86 (5), Pro 5.17 (5), Gly 4.15 (4), Ala 6.09 (6), Cys 3.51 (6), Val 2.86 (3), Met 0.70 (1), Ile 0 (0),Leu 5.74 (6), Tyr 2.12 (2),Phe 0.98 (1), His 2.00 (2),Lys 1.26 (1), Trp 1.00 (1), Arg 5.02 (5). (overall yield 14.9%).

The mobile phase of all HPLC systems used consisted of 0.1% trifluoroacetic acid in water (solvent A) and 0.1% trifluoroacetic acid in 80% acetonitrile (solvent B).

For preparative HPLC, a Waters HPLC system consisting of two pumps (model 6000A) and gradient programmer (model 680) was used in combination with a Synchropak RP-P column (C18) (SynChrom, In) and an Uvicord S UV (226 nm) monitor (LKB, Bromma Sweden). Usually 1 to 20 mg of peptide was separated using linear gradients as indicated.

Analytical HPLC I was performed on Aquapore 300 ($C_8$;2.1 mm×30 mm) using an Applied Biosystems HPLC model 130A. Separation was achieved with a linear gradient from 23% to 34% B in 60 min at a flow rate of 0.1 ml/min. The peptide was detected by UV absorbance at 230 nm.

Analytical HPLC II was performed on Synchropak RP-P (C18, 4.1 mm×250 mm) using a Waters HPLC 20 system. Separation was achieved with a linear gradient from 20% B to 50% in 30 min at a slow rate of 1 ml/min. The peptide was detected by UV absorbance at 220 nm. The above-described HPLC may also be used to verify the purity of the RLF, as set forth in FIG. 3.

The primary structure of RLF, as synthesized according to the above procedure, or any other solid phase methodologies in combination with site-directed sequential disulfide bond formation (a schematic depicting said formation is set forth at FIG. 2), is set forth at FIG. 1.

Protein Confirmation And Verification. The identity of the synthesized RLF may be confirmed and verified according to known techniques.

Amino Acid Analyses: Following protein synthesis and purification, amino acid analyses was conducted to confirm the protein's identity. First, peptides were hydrolyzed in vapor phase 6N HCI containing 0.1% phenol for 1 h at 150° C. The amino acids were detected after pre-column modification with phenylisothiocynate and separation by HPLC (Pico•Tag system, Waters Millipore).

Sequence Analyses: The identity of the protein was verified by sequence analysis. Specifically, such analyses were performed on an ABI 477 A pulsed liquid protein sequencer and an in-line ABI 120A phenylthiohydantoin analyzer (ABI, Applied Biosystems, Foster City, Calif.). Chains were prepared by reduction of about 10 µl of the relaxin-like factor in 20 µl 50 mM DTT in 3 M guanidinium chloride, 0.2 M Tris, HCI at pH 8.5 for 1 h at 37° C., diluted with 30 µl of solvent A, followed by separation on Aquapore 300 (see: Analytical HPLC for conditions).

Upon reduction two chains were generated, isolated, and the subsequent sequence analyses of both chains showed the desired structure.

UV Spectroscopy: The confirmation and structure of the synthesized protein was then confirmed by UV spectroscopy. Such spectroscopy was performed on an OLIS Cary 15 spectrophotometer conversion (On-Line Instrument Systems Inc., Bogart, Ga.). UV-spectroscopy was used to determine the protein concentrations of the RLF protein. The specific absorption coefficient ($\epsilon_{276}$=1.40 cm$_2$/mg) was obtained by direct comparison of UV absorbance and the recovery of amino acids after hydrolysis and amino acid analysis.

No partial hydrolysis at the acid labile Asn-Pro bond was detected.

Circular Dichroism: Further confirmation of the synthesized protein's identity was performed by CD spectroscopy, as performed on a Jasco J-710 spectropolarimeter using a cell of 0.02 cm path length. Proteins were dissolved in 25 mM Tris/HCI at pH 7.7 and concentrations were determined by UV spectroscopy: 0.67 mg/ml for porcine relaxin, 0.54 mg/ml for relaxin-like factor, and 0.55 mg/ml for human relaxin. Spectra were measured at a resolution of 0.2 nm, a band width of 2 nm, and 5 spectra were averaged. Molar ellipticity was calculated according to Adler et al. (9) using mean residual weights of 110.4 for relaxin-like factor, 113.6 for porcine relaxin, and 112.5 for human relaxin.

Comparative measurements of circular dichroic spectra suggested near identity of the solution structures of RLF and porcine relaxin. See, FIG. 4.

Mass Spectrometry: Finally, mass spectra were recorded on a JEOL HX110/HX110 4 sector tandem mass spectrometer (JEOL, Tokyo, Japan) to verify the protein's identity and proper synthesis. Samples were dissolved in 0.1% trifluoroacetic acid at a concentration of about 0.8 nmol/µl.

Mass spectrometry showed the correct mass ion for the synthetic RLF (found: 6294.6, theoretical 6293.2).

6.2. Production Of Labelled RLF $^{125}$I-labeled RLF, containing side chain-protected tryptophan and methionine, may be prepared according to the above procedure wherein the synthesized peptide (10 µg in 5 µl of water) is then placed into a 200 µl Eppendorf vial and 5 µl phosphate buffer (250 mM, pH 7.4), followed by 2 µl of 125I-(1 mCi), and 5 µl of chloramine T (2 mg/ml in phosphate buffer pH 7.4) are added. The reaction was performed for 1 min on ice, quenched by addition of 5 µl of sodium thiosulfate (5 H$_2$O) (50 mg/ml in phosphate buffer pH 7.4), and 5 µl of NaI (20 mg/ml in phosphate buffer pH 7.4). The side chain-protecting group of Trp was removed by addition of 5 µl of piperidine. After 2 min at room temperature the reaction was quenched by the addition of 5 µl of glacial acid, the reaction mixture was diluted with 10 µl of water and loaded onto a Aquapore 300 column for separation. The protein was detected by UV absorbance and peaks were manually collected into 100 µl of 1% bovine serum albumin in water.

The labelled RLF may be used as an RLF tracer which could then be used to separate by HPLC the different RLF derivatives to yield a carrier-free tracer. See, FIG. 5. Alternatively, such labelled RLF may also be used in binding assays and for RLF receptor mapping.

6.3. Receptor Binding Assay

Insulin-receptor binding assays were performed on crude membrane preparations of term placenta, as described in Hock and Hollenberg, 1980, J. Biol. Chem. 255:10731–10736, using $^{125}$I-iodo-Tyr$^{A14}$ porcine insulin as tracer according to the method of Linde, et al., 1986, J. Chromatogr. 369:327–339.

The assays were performed in HMS-buffer (25 mM HEPES, 104 mM NaCl, 5 mM MgCl$_2$, 0.2% bovine serum albumin; pH 7.4) in a total volume of 100 µl. Labeled insulin (50,000 cpm/assay, 150 pM) and variable amounts of insulin were incubated with crude membranes for 1 h at room temperature. Thereafter 1 ml of buffer was added, the membranes collected by centrifugation in a microcentrifuge at 14,000 rpm for 5 min, the supernatant discarded, and the tip of the Eppendorf vial cut off and counted in a γ-counter (Minigamma, LKB,Sweden). To determine nonspecific binding unlabeled insulin was used at a concentration of 2 µl/ml (0.33 µM) and nonspecific binding was usually below 10% of the total binding.

Contrary to prior art speculation, RLF does not bind with any significant degree to the insulin receptor.

6.4. Relaxin-Binding Assays

Relaxin-binding assays were performed as described in Yang, et al., 1992, Endocrinology 130:179–185 and B üllesbach, et al., 1994, Endocrine. 2:1115–1120, using crude membrane preparations of mouse tissue. Mouse brains of 2 mice were collected into 15 ml of chilled buffer (25 mM HEPES, 0.14 M NaCl, 5.7 mM KCI, 0.2 mM phenylmethylsulfonylfluoride, and 80 mg/ml soybean trypsin inhibitor, pH 7.5) supplemented with sucrose (0.25 M, final concentration). The tissue was homogenized on ice for 10 s with a Polytron homogenizer (Brinlmann, Westbury, N.Y.) at setting 5. The homogenate was centrifuged at 700 rpm for 10 min at 4° C. and the supernatants were recentrifuged at 10,000×g for 1 h. The pellet was resuspended in 15 ml of ice cold binding buffer, 25 mM HEPES, 0.14 M NaCl, 5.7 mM KCI, 0.2 mM phenylmethylsulfonylfluoride, and 80 mg/ml soybean trypsin inhibitor, pH 7.5, supplemented with 1% bovine serum albumin, and centrifuged for 1 h at 10,000×g. The crude membrane preparation was suspended in 1 ml of binding buffer and 40 µl was used per assay. The assay was performed using 40 µl of tracer (about 100,000 cpm of porcine relaxin tracer=150 pM) and 20 µl of relaxin at various concentrations. The assay was incubated for 1 h at room temperature, and the suspension diluted with 1 ml of wash buffer (25 mM HEPES, 0.14 M NaCl, 5.7 mM KCI, 1% bovine serum albumin, 0.01% NaN$_3$) and centrifuged in Eppendorf centrifuge at 14,000 rpm for 10 min. The supernatant was discarded, the tip of the vial cut and counted in a γ-counter. Nonspecific binding was determined in the presence of 2 μl/ml of unlabeled competitor (0.33 μM). In a typical experiment the specific binding was between 25% and 40% of the total binding.

Tissue specificity was determined using crude membrane preparations of leg muscles, kidneys, liver. brain, and uterus (of estrogen primed mice). The crude membranes were prepared as described for relaxin. Binding was based on protein concentration determined by Lowry.

According to the above-described assay, a hundred-fold excess of human RLF displaces 50% of the relaxin tracer from a mouse brain relaxin receptor preparation. The difference in affinity is still within the range of specific binding, i.e., several orders of magnitude better than the binding of insulin or guinea pig relaxin to this receptor (see generally, Büllesbach, et al., 1994, *Endocrine*. 2:1115–1120) indicating that RLF recognizes the relaxin receptor.

As discussed above, this result was surprising because the critical two Arg residues separated by three amino acids sequence in RLF is offset toward the C-terminal end of the B chain by exactly one turn of the helix (See, FIG. 1).

Of the tissues tested with $^{125}$I-RLF as tracer such as brain, uterus, skeletal muscle, kidney and liver, only the brain- and the uterus membrane preparation showed specific binding (See, FIG. 6). These are tissues that also bind relaxin in a competitive and saturable manner. To test for crossreactivity the assays were performed with tracers and competitive cold molecules exchanged. The results from such assay are set forth below at Table 1:

TABLE 1

Relaxin-Binding Assay Results

| Tissue (mouse) | Tracer | Competitor | 50% Binding | Range |
|---|---|---|---|---|
| Brain | pRLX | hRLX | 1 ng | 0.1–2.0 |
| Brain | pRLX | hRLF | 200 ng | 190–220 |
| Uterus | PRLX | hRLX | 1 ng | 0.1–2 |
| Uterus | PRLX | hRLF | 10000 ng | — |
| Uterus | hRLF | hRLX | 800 ng | 600–1000 |
| Uterus | hRLF | hRLF | 0.3 ng | 0.1–0.6 |
| Brain | hRLF | hRLX | 1000 ng | 900–1100 |
| Brain | hRLF | hRLF | 0.3 ng | 0.1–0.6 | pRLX = porcine relaxin, hRLX = human relaxin, pRLF = porcine RLF and hRLF = human RLF These results suggest strongly that RLF does have its own receptor in these tissues and that the relaxin receptor is recognized by RLF, but with a significantly lower affinity than relaxin. Furthermore, the data support that the brain and uterine relaxin receptors differ with respect to crossreactivity. Specifically, the uterine relaxin receptor barely recognizes RLF whereas the brain receptor shows moderate crossreactivity. In general, the RLF receptor binds its substrate with greater affinity than the relaxin receptor displays toward relaxin.

6.5. Sperm Motility Assay

Relaxin and proteins having relaxin-like activity may be identified by a sperm motility assay.

Materials And Methods. Semen is obtained by masturbation from healthy volunteers. The sample is allowed to liquefy at room temperature and is then mixed with Minimum Essential Medium (MEM) with Hepes buffer added. This medium is used because it coincides with that washing medium employed by the in vitro clinic at MUSC. The sperm is then separated from the seminal fluid and MEM by centrifugation. The resultant sperm pellet is then resuspended in MEM at room temperature. Aliquots are then place in siliconized centrifuge tubes and one of several compounds added: 1)human relaxin 10 ng/ml, 2)human relaxin 100 ng/ml, 3)relaxin-like factor 10 ng/ml, 4)relaxin-like factor 100 ng/ml, 5)one fraction of alkaline gland fluid from stingrays diluted 1:8 with pentoxyfyline. The additive is mixed well with the sperm/medium mixture. Samples are taken at 0, 2, 4, 6 and 24 hour intervals for automated determination of the following parameters: 1)motility, 2)progressivity, 3)path velocity, 4)progressive velocity, 5)track speed, 6)elongation, 7)lateral displacement, 8)cross beat frequency, 9)straightness, 10)linearity. Briefly described, each sample is loaded into a Maker heated specimen chamber and viewed in a light microscope equipped with laser doppler optics (IVOS, Beverly, Mass.). Sample readings taken at approximately 3 minutes and results are displayed in hard copy form.

Experimental Results. Human relaxin and RLF added to washed human sperm preserve the motility compared to untreated controls in which motility and thus potential fertilizing capacity significantly declines over time. There was essentially no difference between the high and low doses of relaxin in their effects on motility. RLF was as potent in maintaining sperm motility at both doses as was relaxin. The most striking effect of both compounds occurred at 4 hours when motility remained the same or increased from the previous time period.

Both relaxin and relaxin-like factor were given in combination to determine if there was an additive effect. No such effect was observed.

All the above compounds were compared against stingray alkaline gland fluid (ALG) from the HPLC. AGF significantly increased then maintained sperm motility for the first two time periods then was approximately 10% higher for the last three time periods.

6.6. In Vitro Inhibition Of Collagen and Fibronectin Expression By Human Lung Fibroblasts Whether RLF inhibits collagen and fibronectin expression has been studied in the context of human lung fibroblasts. Specifically, RLF (1–100 ng/ml) was applied to human lung fibroblasts in serum-free medium and assayed for collagen secretion by biosynthetic labelling with $_3$H-proline in the presence of ascorbate and B-aminopropionitrile. When tested on lung fibroblasts stimulated with TGF-β, RLF's ability to inhibit collagen expression at various dose levels can be determined. The presence of another extracellular matrix molecule, fibronectin, in conditioned media was assessed by Western immunoblotting using an anti-fibronectin polyclonal antibody, as well as biosynthetic labeling.

6.7. In Vitro Inhibition Of Collagen and Fibronectin Expression By Synovial Fibroblasts Trauma to the shoulder or surgical intervention of large joints is often associated with limitation in mobility, in many cases due to an exaggerated fibrotic response to synovial or capsular tissue. Extracellular matrix-producing cells, such as synovial fibroblasts, are capable of the extremes of degradation or repair. The overproduction of collagens, fibronectin and other extracellular matrix molecules can be due to the local expression of cytokines, such as transforming growth factor TGF-β. To the extent it has been demonstrated that relaxin can decrease TGF-β-stimulated collagen expression in a dose-dependent manner, up to 30% at a relaxin does of 100 ng/ml and fibronectin expression by 30%, RLF is also implicated in the modulation and control of collagen and fibronectin expression.

To test such hypothesis (to determine RLF's ability to down-regulate collagen and fibronectin expressed by synovial fibroblasts), fibroblasts can be explanted from pieces of rheumatoid synovium and treated with TGF-beta (1 ng/ml) to stimulate expression of types I and III collagens. TGF-beta upregulated collagen expression at the protein level, as measured by biosynthetic labelling with 3H-proline incorporation. More specifically, the following experiments were conducted to determine RLF's ability to modulate the expression of collagen, fibronectin and procollegenase in human synovial fibroblasts:

6.7.1. Assay To Determine The Inhibition Of Collagen Expression

The method for detecting and measuring collagen formation in the presence of relaxin described in Unemori and Amento, 1990, *J. Biol. Chem.* 265:10681–685 has been modified as follows to determine the ability of RLF, in vitro, to modulate the expression of collagen.

Materials And Methods. Rheumatoid synovial fibroblasts (Strain No. RSF64) were seeded at a density of 6.25×104 cells/cm$^2$ in tissue culture dishes in Dulbecco's Modified Eagle's Medium (DMEM) supplemented with 10% fetal bovine serum. After 24 hours, the cells were washed and treated with DMEM supplemented with 0.2% lactalbumin hydroxylsate with relaxin, RLF and/or transforming growth factor (TGF-β).

The cells were simultaneously biosynthetically labelled with $^3$H=proline (25 μCi/ml) in the presence of ascorbate and BAPN. After 24 hours, the conditioned media were collected and electrophoresed on 4–12% polyacrylamide gels (NOVEX) under reducing conditions. Gels were enhanced, dried, and exposed to X-ray films for 1–2 weeks. Collagen bands were identified on the X-ray films as bacterial collagenase-sensitive, proline-incorporating bands between 95–200 kDa. Band density was quantified by scanning densitometry and used as estimates of collagen expression.

Experimental Results. Using the above protocol, it was determined that RLF decreases collagen expression independently. Specifically, fibroblast treatment with TGF-β increased collagen expression by 3.75 fold over that expressed by untreated fibroblasts. Subsequent addition of RLF (100 ng/ml) to the TGF-β-treated fibroblasts decreased TGF-β-stimulated collagen expression by 17%. In comparison, addition of relaxin (100 ng/ml) decreased TGF-β-stimulated collagen expression by 9%.

It was further determined that RLF and relaxin together synergistically decrease collagen expression. Specifically, treatment of TGF-β-stimulated cells with RLF (100 ng/ml) and relaxin (100 ng/ml) decreased collagen expression by 39%.

6.7.2. Assay To Determine The Inhibition Of Fibronectin Expression

The method for detecting and measuring collagen formation in the presence of relaxin described in Unemori and Amento, 1990, *J. Biol. Chem.* 265:10681–685 has been modified as follows to determine the ability of RLF, in vitro, to modulate the expression of fibronectin.

Materials And Methods. Specifically, using the method described in section 6.7.1., the fibronectin band was identified by size (220 kDa), bacterial collagenase-resistance, and positive staining using commercially available polyclonal anti-fibronectin antibody (Promega). The fibronectin band was scanned densitometrically to estimate levels of expression.

Experimental Results. Using the above protocol, it was determined that RLF decreases fibronectin expression independently. Specifically, addition of RLF (100 ng/ml) to the TGF-β-treated fibroblasts decreased TGF-β-stimulated fibronectin expression by 17%.

6.8. In Vitro Stimulation Of Procollagense Expression By Synovial Fibroblasts

A method for detecting and measuring procollagenase formation is described in Unemori, et al., 1991, *J. Biol. Chem.* 266:23477–482. Such method was modified to measure the expression of procollagenase in the presence of RLF as follows:

Materials And Methods. Rheumatoid synovial fibroblasts (Strain No. RSF112) were seeded at a density of 6.25×10$^4$ cells/cm$^2$ in tissue culture dishes in DMEM supplemented with 10% fetal bovine serum. After twenty-four hours, the cells were washed and treated with DMEM supplemented with 0.2% lactalbumin hydroxylate with relaxin at 1, 10 and 100 ng/ml for 48 to 72 hours. Conditioned media were collected and an aliquot analyzed by gelatin zymography. Procollagenase was identified as a gelatinlytic doublet at 52/57 kDa. The intensity of the doublet (i.e., the amount of procollagenase expressed, was quantified by scanning densitometry.

Experimental Results. RLF stimulated expression of procollagenase in a dose-dependent manner comparable to that induced by relaxin. RLF at 1, 10 and 100 ng/ml stimulated procolleganse expression by 0, 2.0 and 4.2-fold. Relaxin induced procollagenase expression by 0, 1.6 and 4.9-fold at the equivalent doses.

6.9. Cyclic AMP-Release Bioassay

The cAMP assay is a competitive immunoassay commercially available through Amersham Corporation.

Materials and Methods. To determine cAMP release induced by RLF, normal human endometrial cells are grown at 1.2×10$^4$ cells/well in a 96-well plate in DMEM/F12+10% newborn calf serum. 24 hours later, the cells are washed in serum-free medium comprised of DMEM/F12+0.2% lactalbumin hydrolysate. 24 hours later, the cells are treated with relaxin and/or RLF in the presence of isobutylmethylxanthine and forskolin for 30 min. The cell lysates are harvested with 0.1N HCL, neutralized with 0.1N NaOH, then assayed in the immunoassay (Amersham Corp).

Experimental Results. When relaxin was assayed at 0.78 ng/ml, 86 pM cAMP was measured in endometrial cell lysates. When RLF (2.5 ug/ml) was simultaneously added, 470 pM cAMP, roughly a 5-fold enhancement in cAMP production, was measured. When a relaxin concentration of 3.12 ng/ml was tested with and without RLF (2.5 μg/ml), a 2-fold enhancement was measurable with relaxin+RLF as compared with relaxin alone.

6.10. Mouse Symphysis Pubis Assay

Mouse interpubic ligament assays were performed essentially as described by Steinetz, et al., 1960, *Endocrinology* 67:102–115. Ovariectomized virgin female mice were printed with 5 μg estrogen cypionate in 100 μl sesame oil. Five days later the mice were injected subcutaneously with human relaxin, RLF, or mixtures of human relaxin and RLF in 100 μl of 0.1% benzopurpurin 4B. Specifically, groups of five animals received either human relaxin at a suboptimal dose or a mixture of 0.2 μg, 0.4 μg and 0.8 μg human relaxin and 5 μg of RLF as given in FIG. 8. For negative control 100 μl of 0.1% benzopurpurin 4B in water were injected. After 16 hours the mice were killed in an atmosphere of $CO_2$, the symphysis pubis dissected free, and the distance between theinterpubic bones measured with a dissecting microscope fitted with transilluminating fiber optics.

The RLF significantly increased the activity of human relaxin in the mouse bioassay. Increasing RLF concentrations in the presence of 0.5 μg of human relaxin showed that 5 μg of RLF was optimal (FIG. 9). Again the effect of the RLF is clearly recognized. In the next assay relaxin alone, RLF alone, and a maximal dose of both are compared (FIG. 7). While RLF alone had no effect, the relaxin effect at maximal dose was still augmented by RLF.

The present invention is not to be limited in scope by the exemplified embodiments which are intended as illustrations of single aspects of the invention, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited within the body of the instant specification are hereby incorporated by reference in their entirety. In addition, the publications listed below are of interest in connection with various aspects of the invention and are incorporated herein as part of the disclosure:

1. Adham, et al., 1993, *J. Biol. Chem.* 268:26668–26672;
2. Adler, et al., 1973, *Methods Enzymol.* 27:675–735;
3. Búllesbach, et al., 1994, *Endocrine.* 2:1115–1120;
4. Búllesbach and Schwabe, 1994, *J. Biol. Chem.* 269:13124–13128;
5. Búllesbach and Schwabe, 1993, *Biochem. Biophys. Res. Commun.* 196:311–319;
6. Búllesbach and Schwabe, 1992, *J. Biol. Chem.* 267:22957–22960;
7. Búllesbach and Shcwabe, 1991, *J. Biol. Chem.* 266:10754–10761;
8. Búllesbach, et al., 1980, *Hoppe Seyler's Z. Physiol. Chem.* 361:865–873;
9. Burkhardt, et al., 1994, *Genomics* 20:13–19;
10. Eddie et al., 1986, *Lancet* 1:1344–1346;
11. Eigenbrot, et al., 1991, *J. Mol. Biol.* 221:15–21;
12. Ellman, 1959, *Arch. Biochem. Biophys.* 82:70–77;
13. Hock and Hollenberg, 1980, *J. Biol. Chem.* 255:10731–10736;
14. Linde, et al., 1986, *J. Chromatogr.* 369:327–339;
15. Loumaye et al., 1978, *Gynecologic and Obsteric Investigation* 9:262–267;
16. Olefsky, et al., 1982, *Ann. NY Acad. Sci.* 380:200–216;
17. Rembiesa, et al., 1993, *Endocrine J.* 1:263–268;
18. Schwabe and Búllesbach, 1994, *FASEB J.* 8:12;
19. Schwabe and Harmon, 1978, *Biochem. Biophys. Res. Commun.* 84:374–380;
20. Sherwood et al., 1980, *Endocrinology* 107:691–698;
21. Sherwood and Crnekovic, 1979, *Endocrinology* 104:893–897;
22. Sieber, et al., 1977, *Helv. Chim. Acta* 60:27–37;
23. Steinetz, et al., 1960, *Endocrinology* 67:102–115;
24. Tam, et al., 1991, *J. Am. Chem. Soc.* 113:6657–6662;
25. Tashima, et al., 1995, *J. Clin. Endocrinal. Metab.* 80:707–710; and
26. Yang, et al., 1992, *Endocrinology* 130:179–185.

What is claimed:

1. A pharmaceutical composition comprising a pharmaceutically acceptable excipient and relaxin like factor comprising an A chain and a B chain, said A chain having the amino acid sequence: Ala-Ala-Ala-Thr-Asn-Pro-Ala-Arg-Tyr-Cys-Cys-Leu-Ser-Gly-Cys-Thr-Gln-Gln-Asp-Leu-Leu-Thr-Leu-Cys-Pro-Tyr (SEQ ID NO:3) or said amino acid sequence (SEQ ID NO:3) truncated by up to about 6 amino acids from the N-terminus and/or by up to 6 amino acids from the C-terminus;

said B chain having the amino acid sequence: Pro-Thr-Pro-Glu-Met-Arg-Glu-Lys-Leu-Cys-Gly-His-His-Phe-Val-Arg-Ala-Leu-Val-Arg-Val-Cys-Gly-Gly-Pro-Arg-Trp-Ser-Thr-Glu-Ala (SEQ ID NO:4) or said amino acid sequence (SEQ ID NO:4) truncated by up to 5 amino acids from the N-terminus and/or by up to 5 amino acids from the C-terminus;

said A and B chains linked by disulfide bonds between amino acid residue number 11 of SEQ ID NO:3 and amino acid number 10 of SEQ ID NO:4 and relaxin having the amino acid sequence of naturally occurring relaxin or a biologically active fragment of said relaxin.

2. The pharmaceutical composition of claim 1 wherein the amount of said relaxin like factor is 6.25 fold to 25 fold higher than the amount of said relaxin.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 21 amino acids
      (B) TYPE: amino acid
      (C) STRANDEDNESS: single
      (D) TOPOLOGY: unknown (ii) MOLECULE TYPE: protein (xi) SEQUENCE DESCRIPTION: SEQ ID NO:1:

Gly Ile Val Glu Gln Cys Cys Thr Ser Ile Cys Ser Leu Tyr Gln Leu
   1               5                  10                  15

Glu Asn Tyr Cys Asn
             20

(2) INFORMATION FOR SEQ ID NO:2:

(i) SEQUENCE CHARACTERISTICS:
      (A) LENGTH: 24 amino acids
      (B) TYPE: amino acid
      (C) STRANDEDNESS: unknown
      (D) TOPOLOGY: unknown (ii) MOLECULE TYPE: protein (xi) SEQUENCE DESCRIPTION: SEQ ID NO:2:

Gln Leu Tyr Ser Ala Leu Ala Asn Lys Cys Cys His Val Gly Cys Thr
   1               5                  10                  15

```
     Lys Arg Ser Leu Ala Arg Phe Cys
                  20
```

(2) INFORMATION FOR SEQ ID NO:3:

(i) SEQUENCE CHARACTERISTICS:
        (A) LENGTH: 26 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:3:

```
     Ala Ala Ala Thr Asn Pro Ala Arg Tyr Cys Cys Leu Ser Gly Cys Thr
     1               5                  10                  15

Gln Gln Asp Leu Leu Thr Leu Cys Pro Tyr
                  20                  25
```

(2) INFORMATION FOR SEQ ID NO:4:

(i) SEQUENCE CHARACTERISTICS:
        (A) LENGTH: 31 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:4:

```
     Pro Thr Pro Glu Met Arg Glu Lys Leu Cys Gly His His Phe Val Arg
     1               5                  10                  15

Ala Leu Val Arg Val Cys Gly Gly Pro Arg Trp Ser Thr Glu Ala
                  20                  25                  30
```

(2) INFORMATION FOR SEQ ID NO:5:

(i) SEQUENCE CHARACTERISTICS:
        (A) LENGTH: 29 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:5:

```
     Asp Ser Trp Met Glu Glu Val Ile Lys Leu Cys Gly Arg Glu Leu Val
     1               5                  10                  15

Arg Ala Gln Ile Ala Ile Cys Gly Met Ser Thr Trp Ser
                  20                  25
```

(2) INFORMATION FOR SEQ ID NO:6:

(i) SEQUENCE CHARACTERISTICS:
        (A) LENGTH: 30 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:6:

```
     Phe Val Asn Gln His Leu Cys Gly Ser His Leu Val Glu Ala Leu Tyr
     1               5                  10                  15

Leu Val Cys Gly Glu Arg Gly Phe Phe Tyr Thr Pro Lys Thr
                  20                  25                  30
```